(12) United States Patent
Takahashi et al.

(10) Patent No.: US 10,363,153 B2
(45) Date of Patent: Jul. 30, 2019

(54) SUPERFINE POLYESTER FIBER AND TUBULAR SEAMLESS FABRIC

(71) Applicant: ASAHI KASEI FIBERS CORPORATION, Osaka-shi, Osaka (JP)

(72) Inventors: Tetsuko Takahashi, Tokyo (JP); Junichi Kojima, Tokyo (JP); Keiichi Toyoda, Tokyo (JP)

(73) Assignee: ASAHI KASEI FIBERS CORPORATION, Osaka (JP)

( * ) Notice: Subject to any disclaimer, the term of this patent is extended or adjusted under 35 U.S.C. 154(b) by 850 days.

(21) Appl. No.: 14/383,353

(22) PCT Filed: Mar. 12, 2013

(86) PCT No.: PCT/JP2013/056831
§ 371 (c)(1),
(2) Date: Sep. 5, 2014

(87) PCT Pub. No.: WO2013/137263
PCT Pub. Date: Sep. 19, 2013

(65) Prior Publication Data
US 2015/0081004 A1    Mar. 19, 2015

(30) Foreign Application Priority Data
Mar. 13, 2012  (JP) .................. 2012-055681

(51) Int. Cl.
| | |
|---|---|
| *A61F 2/89* | (2013.01) |
| *A61F 2/95* | (2013.01) |
| *A61L 31/06* | (2006.01) |
| *D01F 6/62* | (2006.01) |
| *D03D 15/00* | (2006.01) |
| *A61L 27/18* | (2006.01) |
| *A61L 27/50* | (2006.01) |
| *A61L 31/14* | (2006.01) |

(52) U.S. Cl.
CPC ............... *A61F 2/89* (2013.01); *A61F 2/95* (2013.01); *A61L 27/18* (2013.01); *A61L 27/50* (2013.01); *A61L 27/507* (2013.01); *A61L 31/06* (2013.01); *A61L 31/14* (2013.01); *D01F 6/62* (2013.01); *D03D 15/0061* (2013.01); *D10B 2331/04* (2013.01); *D10B 2509/06* (2013.01); *Y10T 428/1362* (2015.01); *Y10T 428/249921* (2015.04); *Y10T 428/2913* (2015.01)

(58) Field of Classification Search
CPC ... D04H 1/435; A61F 2/06; A61F 2/07; A61F 2/89; A61F 2/86; A61F 2/95; A61F 2/958; A61F 2002/065; A61F 2002/075; A61L 27/50; A61L 31/14; A61L 31/06; A61L 27/507; A61L 27/18; D03D 15/0061; D03D 3/02; D01F 6/62; D01F 6/84; Y10T 428/1362; Y10T 428/2913; Y10T 428/249921; Y10T 442/30; D10B 2509/06; D10B 2331/04; C08L 67/02; A61M 25/0068
USPC ... 623/1.1–1.49, 1.11, 1.15, 1.14, 1.26, 1.33, 623/1.51, 1.54, 921, 900; 428/221, 364, 428/36.1; 442/181; 528/308.1
See application file for complete search history.

(56) References Cited

U.S. PATENT DOCUMENTS

| | | |
|---|---|---|
| 5,474,836 A | 12/1995 | Nishimura et al. |
| 5,637,385 A | 6/1997 | Mizuki et al. |
| 2001/0056299 A1* | 12/2001 | Thompson ............. A61F 2/90 623/1.53 |
| 2008/0188151 A1 | 8/2008 | Yokoi et al. |
| 2013/0041452 A1* | 2/2013 | Fujita ............. D04B 21/16 623/1.13 |

FOREIGN PATENT DOCUMENTS

| | | |
|---|---|---|
| EP | 2 6658 926 A1 | 12/2013 |
| JP | 55-1338 | 1/1980 |
| JP | 55-132708 | 10/1980 |
| JP | 5-23362 | 2/1993 |
| JP | 6-306731 | 11/1994 |
| JP | 07-173713 | 7/1995 |
| JP | 7-258940 | * 10/1995 |
| JP | 8-35116 | 2/1996 |
| JP | 2003-41432 | 2/2003 |
| JP | 2006-132027 | 5/2006 |
| JP | 2008-7870 | 1/2008 |
| JP | 2008-505713 | 2/2008 |
| JP | 2009-150011 | 7/2009 |

(Continued)

OTHER PUBLICATIONS

Machine translation of JP 7-258940, Jun. 2017.*

(Continued)

*Primary Examiner* — Camie S Thompson
(74) *Attorney, Agent, or Firm* — Finnegan, Henderson, Farabow, Garrett & Dunner, LLP

(57) ABSTRACT

Provided is a superfine polyester fiber containing at least 98 wt % of a polyethylene terephthalate component, and characterized by fulfilling the following conditions: (1) the reduced viscosity (ηsp/c) is at least 0.80 dl/g; (2) the total fineness is 7-120 dtex, and the single filament fineness is no more than 0.5 dtex; and (3) the toughness parameter (X) indicated by formula (1) is at least 2.0, the tensile strength is at least 3.5 cN/dtex and the tensile elongation is at least 12%.

$X = (\text{tensile strength} \times \sqrt{\text{tensile elongation}})/(\text{total fineness} \times \text{single filament fineness})$  formula (1).

5 Claims, No Drawings

(56) References Cited

FOREIGN PATENT DOCUMENTS

| JP | 2012-193476 | 10/2012 |
|----|----|----|
| WO | WO 2006/014592 | 2/2006 |
| WO | WO 2006/043517 | 4/2006 |
| WO | WO 2011/075721 | 6/2011 |
| WO | WO 2011/136243 | 11/2011 |
| WO | WO 2012/102311 A1 | 8/2012 |

OTHER PUBLICATIONS

International Preliminary Report on Patentability from the International Bureau dated Sep. 16, 2014, and Written Opinion of the International Searching Authority from the Japanese Patent Office, dated May 14, 2013, for International Application No. PCT/JP2013/056831.

English-language International Search Report from the Japanese Patent Office, dated May 14, 2013, for International Application No. PCT/JP2013/056831.

* cited by examiner

SUPERFINE POLYESTER FIBER AND TUBULAR SEAMLESS FABRIC

TECHNICAL FIELD

The invention relates to a superfine polyester fiber that is suitable as a material for implantation into the human body. The invention further relates to a tubular seamless fabric that is suitable as a fabric for a low-profile (thin) stent graft.

BACKGROUND ART

Polyethylene terephthalate (hereunder abbreviated as "PET") fibers are widely used as constituent materials of implantable medical equipment such as stent graft fabrics and artificial blood vessels.

Stent grafts are discussed here. Conventional treatment for aortic aneurysm has included artificial blood vessel replacement using e-PTFE or PET artificial blood vessels, but because such techniques involve large-scale surgical operation such as thoracotomy or laparotomy they are highly burdensome for the body and are limited in their suitability to the elderly or patients with complications, while the economical burden for patients and medical facilities is also significant due to the need for long-term hospitalization. On the other hand, transcatheter intravascular treatment using "stent grafts" (a method of treatment in which a narrow catheter having a stent graft compressively inserted therein is introduced through the artery at the base of the foot, and the stent graft is opened and fixed at the site of aneurysm, whereby blood flow into the aneurysm is blocked and burst of the aneurysm is prevented), fitted with a tubular fabric (hereunder referred to as "stent graft fabric") in a spring-like metal known as a stent, does not involve thoracotomy or laparotomy, and therefore in recent years its application has been rapidly increasing since physical and economical burden is reduced.

However, because current stent grafts cannot be folded small and can only be inserted into catheters with thick diameters, in many cases they cannot be applied to females and Asians such as Japanese, which have narrower arteries. Given these circumstances, there is increased need for reducing the diameters of stent grafts, and also demand for stent grafts with maximum inner diameters of 50 mm to be insertable into catheters of 18 French (inner diameter of 6 mm) and smaller, for the thorax, for example.

Narrowing of stent grafts can be achieved by modifying the shape of the stent or the filament diameter of the metal, but since stent grafts are basically fixed to the affected area by a system of pressing against the vascular wall by the expanding force of the metal, there has been a limit to the improvement that can be achieved with expanding force by narrowing the filament diameter. On the other hand, narrowing can also be achieved by reducing the thickness of the stent graft fabric. A stent graft fabric employs an e-PTFE film or a PET fiber woven fabric or knitted fabric, and when the thickness of an e-PTFE film is reduced there is a risk of thinning and drawing and burst of the film with time due to expanding force by the stent or blood pressure, and therefore the degree to which e-PTFE can be reduced in thickness is limited. In order to reduce the thickness of the stent graft fabric, therefore, it is effective to reduce the thickness of the PET fiber fabric, and for this purpose it is necessary to reduce the total fineness and single fiber fineness of the PET fibers composing the fabric, or in other words, to use superfine fibers.

The following types of superfine PET fibers have been known in the prior art.

(a) Sea-island Superfine PET Fibers

Sea-island superfine PET fibers are spun as undrawn filaments having a sea-island cross-section, from a plurality of different polymer components such as PET as the island component and copolymerized PET or polyamide as the sea component, using a melting process, and the undrawn filaments are drawn to a draw ratio within the natural drawing range for PET which is the island component, and then the sea component is removed by dissolving with a solvent.

(b) Polymer Blend Superfine PET Fibers

Polymer blend superfine PET fibers are obtained by melt spinning of a mixture of two or more different polymer components that have different solubilities and are poorly compatible, spinning sea-island fibers with one of the polymers microdispersed inside the other, and after spinning, the sea component is removed by dissolution with a solvent, as in (a) above.

(c) Direct-spun Superfine PET Fibers

Direct-spun superfine PET fibers are obtained by melt spinning a PET polymer alone, to obtain undrawn PET fiber, and drawing it.

Because sea-island and polymer blend superfine PET fibers are obtained by removing the sea component polymer by dissolution with a solvent as described above, the solvent or sea component polymer, or even the hydrolyzable monomer of the sea component, can residually adhere onto the superfine PET fibers, and potentially elute into the body. This is a crucial problem from the viewpoint of biological safety, as a material for implantation into the human body. In addition, since sea-island and polymer blend superfine PET fibers have the sea component removed by dissolution with a solvent after being formed into a fabric, gaps form in the textile structure, and when it is used as a stent graft fabric, for example, endoleak can potentially occur at those locations.

On the other hand, PTLs 1 to 3 disclose direct-spun superfine PET fibers obtained by direct melt spinning methods. Such direct-spun superfine PET fibers do not carry the risk of residue, and can be considered highly safe materials for biological use. However, when conventional direct-spun superfine PET fibers are compared to PET fibers of normal thickness (hereunder referred to as "regular PET fibers"), their strength has been found to be reduced. This is because in a conventional direct melt spinning method it is necessary to minimize the melt viscosity of the polymer until it reaches the spinneret, in order to accomplish continuous stable spinning, and since a starting polymer with a low polymerization degree is used for this purpose, lower strength has been exhibited compared to regular PET fibers. In the case of superfine fibers, non-homogeneity of cooling of the melting filaments discharged from each spinneret results in considerable effects of fiber size variation between filaments or in the fiber axis direction and results in a structure with poor expression of strength, with the tensile strength of the direct-spun superfine PET fibers described in PTLs 1 to 3 having been at most about 3 cN/dtex.

In the case of a stent graft, the high expanding force of the stent (spring-like metal) reaches the fabric when the stent graft is opened from a catheter at the affected blood vessel. The stent graft is also exposed to the conditions of the load of normal blood pressure. Using the superfine PET fibers with low strength described in PTLs 1 to 3, in consideration of the requirement for a stent graft fabric to have sufficient strength to withstand the high expanding force of a stent (spring-like metal) and to withstand the load of blood pressure, and specifically a burst strength of 100N or greater based on ANSI/AAMI, such fibers having a tensile strength of about 3 cN/dtex cannot form a fabric that meets this requirement.

Furthermore, in the case of a stent graft being used as a substitute material for a blood vessel, lack of endoleak is an essential feature and the woven texture must be highly dense, in the case of weaving, for example, in order to form a fabric with no endoleak. Nevertheless, the direct-spun superfine PET fibers described in PTLs 1 to 3 produce yarn breakage or fluff during processing even when forming a sheet-like woven fabric, making it difficult to achieve high density, and in particular it has been extremely difficult to realize high density with tubular seamless fabrics.

For these reasons, it has not yet been possible to obtain excellent biological safety for the constituent fibers of fabrics for low profile stent grafts, or to obtain superfine polyester fibers that are both fine and strong. Moreover, it is currently the case that no fabric has been obtained that exhibits both thinness and strength satisfying the requirements for low profile of stent grafts.

CITATION LIST

Patent Literature

[PTL 1] Japanese Unexamined Patent Publication SHO No. 55-1338
[PTL 2] Japanese Unexamined Patent Publication SHO No. 55-132708
[PTL 3] Japanese Unexamined Patent Publication No. 2006-132027

DISCLOSURE OF THE INVENTION

Problems to be Solved by the Invention

It is an object of the present invention to provide superfine PET fibers that can be used to compose a fabric having the necessary high biological safety and burst strength for a material for implantation into the human body, and that also has high molding workability, and to provide a tubular seamless fabric exhibiting high biological safety, low thickness and sufficient burst strength.

Means for Solving the Problems

As a result of much diligent study and experimentation, the present inventors have completed this invention upon finding that the problems associated with fibers of the prior art can be solved by a polyester fiber containing essentially no components other than PET, and having strength as well as both fineness and toughness.

Specifically, the present invention is as follows.

[1] A superfine polyester fiber having a polyethylene terephthalate component content of 98 wt % or greater, and satisfying the following conditions:
(1) a reduced viscosity ($\eta sp/c$) of 0.80 dl/g or greater,
(2) a total fineness of between 7 dtex and 120 dtex, inclusive, and a single filament fineness of 0.5 dtex or smaller, and
(3) a toughness parameter X of 2.0 or greater as represented by the following formula (1):

$$X = (\text{tensile strength} \times \sqrt{\text{tensile elongation}})/(\text{total fineness} \times \text{single filament fineness}) \quad \text{Formula (1)},$$

a tensile strength of 3.5 cN/dtex or greater and a tensile elongation of 12% or greater.

[2] A superfine polyester fiber according to [1] above, further satisfying the following condition:
(4) For each of 10 sampled fiber bundles, where 10 fiber bundles of 1 cm are sampled at equal spacings of 3 m in the yarn length direction, the interfilament variation $Y_{(1-10)}$ represented by the following formula (2):

[Formula 1]

$$Y_{(1\sim10)} \sqrt{\frac{\Sigma(d_i - d_{av})^2}{(n-1)}} \quad (2)$$

{wherein n is a number of filaments corresponding to at least 30% of the total number of filaments from each of 10 fiber bundles, the yarn diameter $d_i$ is the diameter of each yarn among n filaments corresponding to at least 30% of the total number of filaments from each of 10 fiber bundles, and $d_{av}$ is the average for n filaments} is 0.5 or less for all.

[3] A fabric comprising at least 20 wt % of a superfine polyester fiber according to [1] or [2] above.

[4] A stent graft fabric comprising at least 20 wt % of a superfine polyester fiber according to [1] or [2] above.

[5] An artificial blood vessel comprising at least 20 wt % of a superfine polyester fiber according to [1] or [2] above.

[6] An artificial fiber fabric comprising at least 20 wt % of a superfine polyester fiber according to [1] or [2] above.

[7] A tubular seamless fabric comprising 20 wt % or greater of a superfine polyester fiber with a total fineness of between 7 dtex and 120 dtex, inclusive, and a single filament fineness of 0.5 dtex or smaller, the tubular seamless fabric satisfying the following conditions:
(a) the thickness of the tubular seamless fabric is between 10 μm and 90 μm, inclusive,
(b) the outer diameter of the tubular seamless fabric is between 6 mm and 50 mm, inclusive,
(c) the water permeability before and after needle puncture is 300 cc/cm²/min or less, and
(d) the burst strength is 100N or greater.

[8] A tubular seamless fabric according to [7] above, wherein the tubular seamless fabric is a plain weave structure.

[9] A stent graft employing a tubular seamless fabric according to [7] or [8] above.

[10] A catheter in which a stent graft according to [9] above is inserted.

[11] A stent delivery device comprising a stent graft according to [9] above as a component thereof.

Effect of the Invention

The superfine polyester fiber of the invention does not involve the concerns regarding sea component-derived or solvent-derived residue that are associated with sea-island superfine PET fibers or polymer blend-type superfine PET fibers, and it can therefore ensure the necessary biological safety as a material for implantation into the human body. Also, because the superfine polyester fiber of the invention has fineness (both total fineness and single filament fineness) and high toughness, it allows both thin fabrics and burst strength to be obtained, so that demands for thinness and high burst strength of stent graft fabrics can be met. In addition, since a superfine polyester fiber of the invention has low variation in fiber size between monofilaments, there is no generation of yarn breakage or fluff during textile processing steps and it is possible to provide a high-quality stent graft fabric or artificial blood vessel with high productivity. Also, a tubular seamless fabric composed of the superfine polyester fiber of the invention has a small thickness and sufficient burst strength, and also low water permeability before and after needle puncture. A tubular seamless fabric composed of the superfine polyester fiber of the invention can also be effectively utilized in practice as a stent graft fabric because of its high biocompatibility.

BEST MODE FOR CARRYING OUT THE INVENTION

The superfine polyester fiber of the invention must have a PET component content of 98 wt % or greater, or in other words a content of less than 2 wt % of components other than PET. Here, "components other than PET" refers to components incorporated into the molecular chain by copolymerization or the like, or copolymerized PET, polyamide or polystyrene adhered onto the surfaces of polyester fibers, sea component polymers used for production of sea-island superfine PET fibers, such as polyethylene and polyvinyl alcohol, and decomposition products of these sea component polymers. According to the invention, components other than PET do not include PET-derived monomers and oligomers such as ethylene glycol, terephthalic acid (TPA), monohydroxyethylene terephthalate (MHET) and bis-2-hydroxyethyl terephthalate (BHET). If the content of components other than PET is 2 wt % or greater, the components will elute out into the body when embedded, potentially causing heat release or heterogenization reactions. The content of components other than PET in the superfine polyester fiber is preferably less than 1 wt %, more preferably less than 0.5 wt % and most preferably zero.

The reduced viscosity of the superfine polyester fiber of the invention must be 0.80 dl/g or greater. If the reduced viscosity of the superfine polyester fiber is less than 0.80 dl/g, the tensile strength of the superfine polyester fiber will be below 3.5 cN/dtex, making it impossible to obtain a fabric with the target stent graft fabric burst strength of 100N or greater. From the viewpoint of exhibiting strength by the superfine polyester fiber, the reduced viscosity of the superfine polyester fiber is preferably 0.82 dl/g or greater and more preferably 0.85 dl/g or greater. There is no particular restriction for the upper limit of the reduced viscosity of the superfine polyester fiber of the invention, on the other hand, but the reduced viscosity of the polyester fiber obtained by melt extrusion has a practical limit of 1.50 dl/g, and from the viewpoint of minimizing variation in size between monofilaments, it is preferably no greater than 1.30 dl/g and more preferably no greater than 1.20 dl/g.

The total fineness of the superfine polyester fiber of the invention must be between 7 dtex and 120 dtex, inclusive, from the viewpoint of achieving both thinness and burst strength for a stent graft fabric. The total fineness is the product of the fineness of a single filament and the total number of filaments. The thickest blood vessel in which a stent graft can be used is the thoracic aorta, with usually about 40 to 50 mm as the inner diameter. As mentioned above, for the thoracic aorta it is desirable for a stent graft with a maximum inner diameter of 50 mm to be insertable in a catheter of up to 18 French (6 mm inner diameter), but study by the present inventors to date has shown that the maximum thickness for a tubular fabric with an inner diameter of 50 mm that can pass through a 6 mm diameter hole is 90 µm, and since this thickness does not significantly change even when the inner diameter of the tubular fabric is varied, the standard for the thickness of the fabric is no greater than 90 µm for specifying the superfine polyester fiber of the invention.

If the total fineness of the superfine polyester fiber is less than 7 dtex the thickness of the fabric will be reduced to a suitable low profile required for a stent graft, but it also tends to have poor passage through the processing steps, suffering fluff or yarn breakage during the molding process including the weaving process, and the fabric may also have reduced burst strength. In addition, if the total fineness of the superfine polyester fiber exceeds 120 dtex the thickness of the fabric will exceed 90 µm even if the single fiber fineness is 0.5 dtex or smaller, for example, and it will not be able to pass through a 6 mm diameter hole (assuming a 6 mm inner diameter catheter), when formed into a tubular fabric with an inner diameter of 50 mm, for example. From the viewpoint of achieving both thinness and burst strength for the fabric, the total fineness of the superfine polyester fiber is preferably between 10 dtex and 110 dtex, inclusive, and more preferably between 15 dtex and 100 dtex, inclusive.

On the other hand, the single filament fineness of the superfine polyester fiber of the invention must be no greater than 0.5 dtex from the viewpoint of achieving an extremely thin thickness for a stent graft fabric. The single filament fineness is the size per monofilament. If the single filament fineness exceeds 0.5 dtex, it will be difficult to achieve a thin fabric thickness of less than 90 µm even if the total fineness is 120 dtex or smaller. Also, if the single filament fineness is less than 0.5 dtex, the increased affinity with vascular endothelial cells will promote integration between the vascular wall tissue and the fabric, thus helping to prevent movement and separation of the stent graft inside the vessel. Integration between the vascular wall tissue and fabric will also minimize direct contact of the fabric with body fluids, and can therefore be expected to produce an effect of minimizing hydrolysis in the body and thus leading to prolonged durability in the body. From the viewpoint of thinness and cellular affinity for the fabric, the single filament fineness of the superfine polyester fiber is preferably no greater than 0.4 dtex and more preferably no greater than 0.3 dtex. There is no particular restriction on the lower limit for the single filament fineness, but from the viewpoint of suitability for post-treatment steps such as textile processing and the burst strength of the fabric, it is preferably 0.01 dtex or greater and more preferably 0.03 dtex or greater.

The superfine polyester fiber of the invention has a toughness parameter X of 2.0 or greater as represented by the following formula (1):

$$X = (\text{tensile strength} \times \sqrt{\text{tensile elongation}})/(\text{total fineness} \times \text{single filament fineness}) \quad \text{Formula (1)},$$

a tensile strength of 3.5 cN/dtex or greater and a tensile elongation of 12% or greater.

If the superfine polyester fiber of the invention has a toughness parameter X of 2.0 or greater, it will be possible to achieve both the desired thinness and burst strength for the fabric. If the toughness parameter X of the superfine polyester fiber is less than 2.0, it may be difficult to obtain a thin fabric of 90 µm or smaller or it may be impossible to achieve a fabric burst strength of 100N or greater, even if the reduced viscosity and total fineness or single filament fineness of the superfine polyester fiber, as well as other conditions, are controlled to within the ranges specified by the invention.

The toughness parameter X of the superfine polyester fiber of the invention is preferably 2.5 or greater and more preferably 3.0 or greater, from the viewpoint of achieving both thinness and burst strength.

Also, the superfine polyester fiber of the invention must have a toughness parameter X of 2.0 or greater, as well as a tensile strength of 3.5 cN/dtex or greater and a tensile elongation of 12% or greater. If the tensile strength of the superfine polyester fiber is less than 3.5 cN/dtex the burst strength of 100N or greater desired for the fabric will not be exhibited, and it will not be able to withstand the tension produced during textile processing, resulting in fluff or yarn breakage, and the production efficiency for the fabric will be notably reduced. On the other hand, while increasing the draw ratio for a polyester fiber can increase the tensile strength, even if the tensile strength is increased to 3.5 cN/dtex or greater by drawing, for example, a tensile elongation of less than 12% results in significant generation of fluff or yarn breakage during textile processing, and notably reduces the production efficiency for the fabric. From the viewpoint of stability of the fabric in the weaving steps, the tensile strength of the superfine polyester fiber of the invention is preferably 3.8 cN/dtex or greater and more preferably 4.0 cN/dtex or greater. From the same viewpoint, the tensile elongation of the superfine polyester fiber of the invention is preferably 15% or greater and more preferably 20% or greater.

From the viewpoint of both fineness and high toughness, the superfine polyester fiber of the invention preferably has an interfilament variation $Y_{(1-10)}$ represented by the following formula (2) of 0.5 or lower for all of the filaments.

[Formula 2]

$$Y_{(1 \sim 10)} \sqrt{\frac{\Sigma(d_i - d_{av})^2}{(n-1)}} \quad (2)$$

In formula (2), 1 cm of fiber bundle is sampled at 10 points at equal spacings along 3 m in the yarn length direction ($Y_1$-$Y_{10}$). After removing n filaments corresponding to at least 30% of the total number of filaments from the fiber bundles at the 10 sampling points, each yarn diameter $d_i$ is measured. The average for the n filaments is $d_{av}$. The 10 fiber bundles are measured for yarn diameter by this procedure, and the interfilament variation $Y_{(1-10)}$ is calculated.

A value of 0.5 or smaller for a fiber bundle sample Y sampled at a given point indicates low yarn diameter variation between the monofilaments, and a uniform yarn diameter. Also, a value of 0.5 or less for the interfilament variation $Y_1$-$Y_{10}$ for all of the 10 fiber bundle sampling points indicates low yarn diameter variation in the fiber axis direction, and a fiber with excellent uniformity.

If the interfilament variation $Y_{(1-10)}$ for the superfine polyester fiber is 0.5 or less, generation of fluff or yarn breakage during textile processing is considerably reduced and production efficiency of the fabric is markedly increased. In addition, if the interfilament variation $Y_{(1-10)}$ of the superfine polyester fiber is 0.5 or less, surprisingly, an effect is exhibited of notably increased cell affinity. This effect is associated with a shorter period of integration between vascular wall tissue and the fabric, and can even further prevent movement or separation of the stent graft in blood vessels. While the principle of correlation between the interfilament variation $Y_{(1-10)}$ and cell affinity of the superfine polyester fiber is not fully understood, it is conjectured that since cell affinity increases when the single filament fineness is less than 0.5 dtex, as mentioned above, the fiber size uniformity between monofilaments increases, thereby synergistically increasing the number of cells that bond to the monofilaments as scaffolding. From the viewpoint of achieving both fineness and high toughness, from the viewpoint of improving suitability for the textile processing step, and from the viewpoint of increasing cellular affinity, the interfilament variation $Y_{(1-10)}$ for the superfine polyester fiber is preferably 0.4 or less and more preferably 0.3 or less. Also, the superfine polyester fiber of the invention preferably has a U % of no greater than 2%, as an index of size unevenness in the fiber axis direction. If the U % of the superfine polyester fiber exceeds 2%, variation in the strong ductility will increase, and this can lead to yarn breakage and fluff generation during textile processing. A more preferred range for U % is no greater than 1.8%, and more preferably no greater than 1.5%.

From the viewpoint of integratability between vascular wall tissue and fabric, and from the viewpoint of inhibiting water permeability after needle puncture for use as a stent graft fabric, the superfine polyester fiber of the invention preferably has a microcrimp inflection point of 5/cm or greater. The microcrimp inflection point is the location where there is a condition that is bent, undulating, arc-shaped, coiled, twisted, warped, zigzag, raised, depressed or spiraled, i.e. a non-linear condition of the superfine polyester fiber. For example, when the crimp is coiled, the point of 180° turn from an arbitrary original point is inflection point 1, and the number of inflection points every 180° turn thereafter is counted. If the superfine polyester fiber has at least 5/cm microcrimp inflection points, spaces with sizes easily infiltrated by cells will be formed between the superfine fibers, and the integratability between vascular wall tissue and the fabric will be increased. Also, as explained below in regard to the fabric, a needle penetrates the fabric when the stent and graft are stitched with suture thread, and if the superfine polyester fiber has at least 5/cm microcrimp inflection points, highly bulked fibers will block gaps even when gaps are created in the fabric after needle puncture, and therefore water permeability after needle puncture will be minimized. It is not desirable to have numerous microcrimp inflection points of the superfine polyester fiber, and for example, if they exceed 50/cm, the fiber bundle becomes excessively bulky and can result in fluff and yarn breakage during textile processing. From the viewpoint of shortening the period for integration between vascular wall tissue and the fabric, and minimizing water permeability after needle puncture, and also from the viewpoint of suitability for textile processing steps, the microcrimp inflection points of the superfine polyester fiber are preferably between 7/cm and 40/cm, inclusive, and more preferably between 10/cm and 30/cm, inclusive.

The superfine polyester fiber of the invention can be effectively applied as a material for implantation into the human body, including suture threads, stent graft fabrics, artificial blood vessels, artificial fiber fabrics used in inguinal hernia treatments and the like, antiadhesive agents, prosthetic ligaments, artificial valves and the like, and in addition to materials for implantation into the human body, it may also be effectively applied as an in vitro material for medical use such as a hemofiltration material, cell separating membrane, cell adsorption material or cell culturing substrate. Naturally, since the superfine polyester fiber of the invention has high toughness and low fiber size variation, it can also be utilized for materials other than those in the medical field, such as clothing materials or materials for filtering or wiping.

One use that takes advantage of the thin strong superfine polyester fiber of the invention is as a stent graft fabric which has both thinness and burst strength, while also preventing endoleak. In order to satisfactorily exhibit adequate practical performance as a stent graft fabric, it must be a tubular seamless fabric comprising 20 wt % or greater of a superfine polyester fiber with a total fineness of between 7 dtex and 120 dtex, inclusive and a single filament fineness of 0.5 dtex or smaller, and satisfying the following conditions (a) to (d):

(a) the thickness of the tubular seamless fabric is between 10 μm and 90 μm, inclusive, (b) the outer diameter of the tubular seamless fabric is between 6 mm and 50 mm, inclusive, (c) the water permeability before and after needle puncture is 300 cc/cm²/min or less, and (d) the burst strength is 100N or greater.

From the viewpoint of achieving a thin stent graft fabric, the tubular seamless fabric of the invention must be composed of superfine polyester fiber having a total fineness of between 7 dtex and 120 dtex, inclusive and a single filament fineness of 0.5 dtex or smaller. Also, from the viewpoint of obtaining a thin fabric and exhibiting affinity with cells, the tubular seamless fabric of the invention must comprise the superfine polyester fiber at 20 wt % or greater. If the component proportion ratio of the superfine polyester fiber in the woven fabric is less than 20 wt %, the fabric thickness will exceed 90 μm, and it will be difficult to obtain a fine diameter. Also, if the component proportion ratio of the superfine polyester fiber is less than 20 wt %, no effect of integration of vascular wall tissue and the fabric will be exhibited, and an effect of preventing intravascular movement of the stent graft cannot be expected. The component proportion ratio of the superfine polyester fiber is preferably 30 wt % or greater and more preferably 40 wt % or greater. The materials other than the superfine polyester fiber composing the tubular seamless fabric may be polyester fiber, polyamide fiber, polyethylene fiber, polypropylene fiber or the like, that are not within the scope of the invention. These may be monofilaments or multifilaments, and one type or a combination of two or more types of fiber material may be used according to the purpose, where combinations may be composite fibers comprising polyester fiber of the invention twisted with other fibers, or using other fibers as the warp yarn or weft yarn of a woven fabric, or using them partially in certain sections.

A stent graft fabric may be a sheet-like fabric attached together into a tubular form, but the thickness will increase at the attachment sections and it will not be possible to fold the fabric in a narrow manner. Also, from the viewpoint of preventing endoleak, the stent graft fabric must have a woven fabric structure. Thus, the fabric of the invention must be a tubular seamless fabric from the viewpoint of achieving a low profile for a stent graft and preventing endoleak. The woven fabric structure may be a plain weave, twill weave, satin weave or the like without any particular restrictions, but from the viewpoint of obtaining a thin fabric and preventing endoleak, it preferably has a plain weave structure or twill weave structure. The warp density and weft density of the tubular seamless fabric of the invention is preferably 100/inch or greater and more preferably 120/inch or greater from the viewpoint of preventing endoleak. The upper limit is not particularly restricted but is essentially no greater than 350/inch.

The thickness of the seamless woven fabric of the invention is between 10 μm and 90 μm, preferably between 15 μm and 80 μm and more preferably between 20 μm and 70 μm, from the viewpoint of obtaining a low profile. The thickness of the woven fabric is defined as the average of the measured values for the thickness of the fabric at 10 locations arbitrarily selected within a range in the circumferential direction of the tubular woven fabric (arbitrarily depending on the diameter) and the lengthwise direction (10 cm-30 cm), using a thickness gauge. If the thickness of the fabric exceeds 90 μm, it will not be possible for a tubular woven fabric with an inner diameter of 50 mm, for example, to pass through a hole with a diameter of 6 mm. On the other hand, if the fabric thickness is smaller than 10 μm it will not be possible to maintain sufficient burst strength. For measurement of the thickness of the seamless woven fabric, the values for the thickness variation Z at measurement points, represented by the following formula (3):

$$Z(\%)=(Z_{av}-Z_i)/Z_{av}\times 100 \qquad \text{formula (3)}$$

{where $Z_{av}$ is the average for 10 measured values, $Z_i$ is the measured value at each point and i is an integer of 1 to 10} are all preferably within ±15%.

If the thickness variation is greater than −15%, passage through a 6 mm-diameter hole may not be possible even if the average value for the fabric thickness is 90 μm or smaller. Also, sections with thickness variation exceeding 15% may have low thickness and impaired burst strength and water permeation prevention. The thickness variation Z is preferably within ±12%, and most preferably within ±10%.

The outer diameter of the seamless woven fabric of the invention will depend on the inner diameter of the blood vessel in which the stent graft is to be used, and may be between 6 mm and 50 mm, inclusive.

The tubular seamless fabric of the invention has a water permeability of no greater than 300 cc/cm²/min before and after needle puncture. The water permeability of the fabric is an index of endoleak prevention, and with a water permeability of no greater than 300 cc/cm²/min, endoleak from the fabric wall face will be minimized. On the other hand, the stent graft fabric may be prepared as a final stent graft product sewn together with a metal stent using suture thread, but if large needle holes are opened in the fabric during such a procedure, endoleak may occur at those locations. In other words, the water permeability after puncture of a needle, as practical performance for a stent graft fabric, must be no greater than 300 cc/cm²/min. The water permeability after needle puncture is the value measured after arbitrarily passing a tapered ⅜ needle 10 times through the fabric in a 1 cm² area. Since superfine polyester fiber is used in the tubular seamless fabric of the invention, the monofilaments are pressed flat in the woven texture to fill the gaps at the crossing points of the warp yarn and weft yarn, and the water permeability before needle puncture is kept to a minimum. Also, as regards the water permeability after needle puncture, in a fabric having PET fibers of normal thickness, having single filament diameters of several μm or greater, woven to high density or a strongly calendar pressed fabric, designed to minimize water permeability, the fibers composing the fabric are firmly constrained (mobility of the individual fibers is inhibited), and therefore the fibers are inhibited from returning to their original positions after having moved when the needle passes through, and open needle holes remain after needle puncture. On the other hand, since the tubular seamless fabric of the invention employs superfine polyester fiber composed of numerous superfine filaments, it is resistant to formation of needle holes and the water permeability after needle puncture can be limited to no greater than 300 cc/cm²/min. In addition, if specific microcrimp inflection points are formed in the superfine polyester fiber composing the tubular seamless fabric of the invention, as mentioned above, it will be easier for them to return to their original structure even when the fibers have freedom of mobility between the tangling points of the warp yarn and weft yarn, as is normal even with a fabric having a woven density that inhibits fiber mobility, and the fibers are pressed flat when a needle passes through, and therefore the effect of minimizing water permeability after needle puncture becomes notable. From the viewpoint of practical performance, the water permeability of the tubular seamless fabric of the invention before and after needle puncture is preferably no greater than 250 cc/cm$^2$/min and more preferably 200 cc/cm$^2$/min.

The porosity of a tubular seamless fabric of the invention is preferably between 30% and 95%, inclusive. Forming spaces in at least 30% of the fabric will facilitate infiltration of cells between the superfine fibers and increase integratability between vascular wall tissue and the fabric (exhibiting an effect of preventing endoleak and preventing movement of the stent graft), while also allowing the water permeability after needle puncture to be controlled to no greater than 300 cc/cm$^2$/min. On the other hand, a fabric porosity of greater than 95% may lead to deformation of the fabric, and can result in increased water permeability. The porosity of a tubular seamless fabric of the invention is more preferably between 35% and 90%, inclusive, and more preferably between 40% and 85%, inclusive.

The tubular seamless fabric of the invention must have a burst strength of 100N or greater as measured by a burst strength test according to ANST/AAMI/ISO7198: 1998/2001. If the burst strength of the fabric is less than 100N, this may constitute a problem in terms of safety when used as a stent graft fabric, considering burst by expanding force of the stent, for example, and it is preferably 120N or greater and more preferably 140N or greater. There is no particular restriction on the upper limit for the burst strength of the fabric, but from the viewpoint of balance with thinness of the fabric, it is essentially no greater than 500N.

The tubular seamless fabric of the invention may be coated with collagen, gelatin or the like in a range that is within the conditions of thickness and outer diameter specified by the invention.

The tubular seamless fabric of the invention is used as a stent graft by combination with a stent (spring-like metal) that is to serve as an inflatable member. The type of stent graft may be a tubular simple straight type, or a branched type or fenestrated type suitable for branched blood vessels. An inflatable member may employ a self-inflating material using a shape memory alloy, superelastic metal or synthetic polymer material. An inflatable member may have any design of the prior art. An inflatable member can also be applied as a type that expands with a balloon, instead of a self-inflating type.

A stent graft according to a preferred embodiment of the invention is inserted into a catheter and delivered into a blood vessel. The stent graft of the invention is thin, with a fabric thickness of 90 μm or smaller, with high flexibility, and it can therefore be inserted into a low profile catheter, and consequently can be easily delivered into blood vessels, with low risk of damage to vascular walls. The catheter used is preferably one of the prior art, such as a tube type or balloon type. Also, a stent graft inserted into a low profile catheter for the invention can be delivered into and be indwelling in a blood vessel, using a conventional delivery system. When the tubular seamless fabric of the invention is to be used as a stent graft fabric, the stent graft may have a low profile, and it can therefore reduce the physical and economical burden on patients, such as shortening the inpatient periods, and can reduce risks such as vascular wall damage. In addition, it is possible to widen the range of applications to cases that have hitherto been excluded as targets of transcatheter intravascular treatment, such as females and Asians that have narrower arteries.

The superfine polyester fiber and method for producing a tubular seamless fabric according to the invention will now be explained in greater detail, with the understanding that the invention is not limited to the methods described.

According to the invention, it is preferred to employ a direct melt spinning method in which a polymer composed essentially of polyethylene terephthalate (PET) is melt spun and then drawn to produce a superfine polyester fiber. The melt spinning machine used may be a known spinning machine equipped with a dryer, extruder and spinning head. The molten PET is discharged from a plurality of discharge nozzles in a spinneret mounted on the spinning head, and immediately after spinning it is blasted with cooling air from a cooling device provided under the spinneret surface for cooling to solidification, and spun into a multifilament.

For production of the superfine polyester fiber of the invention, it is preferred to use a PET polymer with a reduced viscosity of 0.85 dl/g or greater from the viewpoint of exhibiting fiber strength and high toughness, but from the viewpoint of spinning stability the upper limit for the reduced viscosity of the starting PET polymer is 1.60 dl/g. From the viewpoint of physical properties and spinning stability of the superfine PET fibers, the reduced viscosity of the starting PET polymer is more preferably between 0.87 dl/g and 1.50 dl/g inclusive, and more preferably between 0.90 dl/g and 1.40, inclusive. The material PET polymer to be used for the invention is preferably produced using a polymerization catalyst other than the heavy metal antimony, from the viewpoint of biological safety. Preferred polymerization catalysts include compounds composed mainly of titanium, such as amorphous titanium oxide and organic titanium, or germanium which is used for polymerization of PET for food packaging films such as PET bottles. The starting PET polymer to be used for the invention preferably has a lower content of crystalline titanium oxide used as a delustering agent, from the viewpoint of preventing elution in the body. Specifically, the amount of titanium element is preferably no greater than 3000 ppm, more preferably no greater than 2000 ppm and even more preferably no greater than 1000 ppm with respect to the polymer weight.

In the method for producing a superfine polyester fiber according to the invention, preferably the spinneret surface temperature during spinning is controlled to a range of between 290° C. and 320° C., and when the discharge nozzle is a multiple array, the spinneret surface temperature distribution (the temperature distribution from the outermost array to the innermost array) is preferably within 10° C. By controlling the spinneret surface temperature to a range between 290° C. and 320° C., it is possible to minimize reduction in molecular weight by thermal decomposition of PET polymers with a relatively high polymerization degree, while simultaneously accomplishing spinning without size unevenness in the fiber axis direction. If the spinneret surface temperature is below 290° C. the pressure of the spinpack will increase, producing melt fracture in the discharged yarn and increasing variation between monofilaments, and making it impossible to exhibit the desired strength. If the spinneret surface temperature exceeds 320° C., it may not be possible to exhibit the desired strength due to lower molecular weight induced by thermal decomposition in the spinpack, and spinneret contamination may render spinning impossible. By controlling the spinneret surface temperature distribution to within 10° C., on the other hand, it is possible to minimize variation in the melt viscosity of the discharge polymer and reduce single filament diameter unevenness between monofilaments (interfilament variation). From the viewpoint of limiting variation in fiber size between monofilaments and size unevenness in the fiber axis direction, and also exhibiting strength, more preferably the spinneret surface temperature is between 295° C. and 310° C., and the spinneret surface temperature distribution is controlled to within 5° C.

There are no particular restrictions on the means for controlling the spinneret surface temperature and the temperature distribution between nozzles to the ranges specified above, but a method of temperature adjustment by surrounding the lower spinneret portion with a heater, or a method of heating adjustment with a heater around the protruding spinneret, may be employed. In either of these methods, it is important to avoid heat from being transferred from the heater to the spinning head, from the viewpoint of inhibiting reduction in polymerization degree by thermal decomposition of the polymer in the spinning head, and from the viewpoint of high strength, high toughness and spinning stability of the superfine polyester fiber. Heat transfer from the heater can be blocked, for example, by not directly mounting the heater on the spinning head and inserting a heat-shielding plate between them, and this method is effective both when temperature adjustment is made by heating the lower part of the spinneret with a surrounding heater, and when heating is carried out around the protruding spinneret. Also, for heating of the protruding spinneret, heating only the protruding spinneret portion with an induction heating system is also effective for preventing heat transfer to the spinning head.

According to the invention, the number of discharge nozzles per spinneret is preferably 20-1500 bored holes. The arrangement of the discharge nozzles is not particularly restricted and may be a circumferential arrangement, crossing arrangement or the like, but for a circumferential, arrangement there are preferably multiple circumferential rows in order to increase the number of nozzles. As mentioned above, according to the invention the discharged yarn is cooled to solidification by blasting cooling air from a cooling device provided below the spinneret surface, but in the case of multiple circumferential rows, depending on the number of filaments and the number of rows, the blasted cooling air may not easily reach the innermost rows due to the influence of company flow, and uneven cooling may occur in the discharged yarn between the outermost rows and the innermost rows, often resulting in high fiber size variation between the monofilaments (interfilament variation). In this case, a nozzle-free area is provided between the outermost rows and innermost rows of the spinneret, so that cooling air can more easily reach the innermost rows. In other words, it is preferred to provide a flow passage for the cooling air, so that cooling solidification of the discharged yarn is accomplished uniformly from the outermost rows to the innermost rows and interfilament variation is reduced. The number of rows in a multiple circumferential arrangement, the distance between rows, the distance between the discharge nozzles on circumferential rows, and the design of the cooling air flow passage may be determined as desired within ranges for the desired filament number and single filament fineness and the allowable spinneret size, but the distance between circumferential rows is preferably between 1 mm and 12 mm, inclusive, from the viewpoint of preventing fusion between the monofilaments and avoiding an excessive spinneret size, and the distance between discharge nozzles on the circumference is preferably between 1.2 mm and 5 mm, inclusive, from the viewpoint of preventing uneven cooling, preventing fusion between the monofilaments, and achieving a suitable spinneret size design.

The hole diameter of the discharge nozzle is preferably between 0.05 mmϕ and 0.1.5 mmϕ, inclusive.

In the method for producing a superfine polyester fiber according to the invention, it is important to provide a hot zone in which the atmosphere temperature above and below the spinneret surface is controlled to 150° C. or higher, and to pass the discharged yarn through it, from the viewpoint of high toughness, in which case the hot zone range is preferably located in a range of between 1 mm and 60 mm, inclusive, from the spinneret surface. The atmosphere temperature is the temperature at a point moved vertically downward at a spacing of 1 mm from the center section of the spinneret surface. Therefore, a hot zone of less than 1 mm cannot be measured. If the hot zone is greater than 60 mm, the yarn may slope and it will be difficult to wind up the filament. Even if the filament can be wound up, the interfilament variation and size unevenness (U %) in the fiber axis direction of the obtained superfine polyester fiber will be poor. Also, if the atmosphere temperature at the point 1 mm from the spinneret surface is not controlled to 150° C. or higher, yarn bending will occur and spinning will not be possible, or even if it is possible, fibers with the desired strength will not be obtained. The hot zone conditions can be adjusted by the thickness and temperature of the heater mounted on the spinneret head, the elevation angle and temperature of the cooling air diffuser, and the thickness of the heat-shielding plate.

The hot zone is preferably within 50 mm and more preferably within 40 mm from the spinneret surface. If the hot zone environment is properly adjusted, it will be possible to use the heater described above for spinneret surface temperature control, and if blowing in of cooling air can be prevented, a heat-shielding plate with a thickness of 60 mm or smaller may be set in the spinning head.

In addition, from the viewpoint of spinning stability and controlling interfilament variation and size unevenness in the fiber axis direction, the discharge yarn is preferably quenched to solidification with a cooling system (described below) after passing through the hot zone, and the atmosphere temperature at the uppermost position of the cooling air blowing surface (a point 1 cm distant from the yarn discharged from the outermost row of the spinneret) is more preferably no higher than 120° C. and most preferably no higher than 100° C.

From the viewpoint of increasing spinning stability and minimizing interfilament variation between the superfine polyester fibers, it is important for the cooling air blowing device to be set surrounding the discharge yarn, and for variation Z in the cooling air speed from the cooling air blowing surface to be reduced. In other words, when the cooling air speed is measured from a specific location on the cooling air blowing surface, over a 360° circumference with a 15° pitch, it is important for the speed variation Z of the cooling air to be no greater than 0.15, where the cooling air speed at the total of 24 points is represented by the following formula (3):

[Formula 3]

$$Z = \sqrt{\frac{\Sigma(X_i - X_{av})^2}{(n-1)}} \quad (3)$$

{where $X_i$ is the data for each cooling air speed, $X_{av}$ is the average value for the 24 points where the cooling air speed is measured, and n is the number of measurements=24}. If the cooling air speed variation Z exceeds 0.15, the yarn may slope and it may become difficult to wind up the filaments, and even if they can be wound up, the obtained superfine polyester fiber will have large yarn diameter variation between monofilaments and the interfilament variation Y as an index of yarn diameter variation between monofilaments will not be 0.5 or lower. From the viewpoint of minimizing interfilament variation of the superfine polyester fiber, the cooling air speed variation Z represented by formula (3) is more preferably no greater than 0.13 and even more preferably no greater than 0.10. In addition, the cooling air speed is preferably between 0.6 m/s and 2.0 m/s from the viewpoint of uniformity of cooling from the outermost rows toward the innermost rows. Here, the cooling air speed is the average value of the cooling air speed measured at a total of 24 points for evaluation of the cooling air speed variation Z. If the cooling air speed is lower than 0.6 m/s it will be difficult for the blasted cooling air to reach the innermost rows, due to the influence of company flow, and cooling unevenness will occur in the discharged yarn between the outermost rows and innermost rows, resulting in increased yarn diameter variation between monofilaments (interfilament variation). If the cooling air speed exceeds 2.0 m/s, on the other hand, the discharged yarn from the outermost rows may undergo swinging, resulting in yarn breakage, interfilament variation, and size unevenness in the fiber axis direction. The cooling air speed is more preferably between 0.7 m/s and 1.8 m/s, inclusive, and most preferably between 0.8 m/s and 1.5 m/s, inclusive. The temperature of the cooling air is preferably controlled to the range of −30° C. or higher and no higher than 18° C., from the viewpoint of quenching solidification and cooling uniformity of the discharged yarn, and it is more preferably −15° C. or higher and no higher than 16°C., and most preferably −10° C. or higher and no higher than 15° C.

In the method for producing a superfine polyester fiber according to the invention, preferably the discharged yarn is bundled at a location between 5 cm and 50 cm from the direct bottom of the spinneret, from the viewpoint of minimizing swinging of the yarn and increasing spinning stability, and it is more preferably between 10 cm and 40 cm, inclusive, and even more preferably between 15 cm and 30 cm, inclusive.

In the method for producing a superfine polyester fiber according to the invention, spinning is preferably carried out at between 300 m/min and 3000 m/min, inclusive, supplying a finishing agent to the fiber bundle after bundling, from the viewpoint of spinning efficiency and high toughness, and this is more preferably between 700 m/min and 2800 m/min, inclusive, and even more preferably between 1000 m/min and 2500 m/min, inclusive. Also, from the viewpoint of bulk finishing and suitability for textile processing, the oil application rate of the finishing agent is preferably between 1 wt % and 3 wt %, inclusive, more preferably between 1.2 wt % and 2.8 wt %, inclusive, and even more preferably between 1.5 wt % and 2.5 wt %, inclusive.

In the method for producing a superfine polyester fiber according to the invention, the undrawn yarn obtained by spinning at the speed mentioned above may be continuously drawn and wound up as a drawn yarn, or it may be first wound up as an undrawn yarn and then drawn on a separate line with a drawing/twisting machine, horizontal drawing machine or the like, and wound up as drawn yarn. In either case, preferably drawing is at a drawing temperature of 50° C. to 120° C. followed by heat treatment at 80° C. to 180° C. and wind-up, for a tensile elongation of 12% or greater.

In the method for producing a superfine polyester fiber according to the invention, tangling treatment at the undrawn yarn stage or drawn yarn stage is preferred from the viewpoint of reducing fluff and yarn breakage during bulking treatment and textile processing, and the tangling treatment preferably employs a known tangling nozzle, with the number of tangles being in the range of 1-50/m. As mentioned above, the superfine polyester fiber of the invention preferably has bulk between the monofilaments to promote infiltration of cells in the spaces between the monofilaments, in which case the preferred method is a water jet or false twisting treatment. With false twisting treatment, for example, twisting is preferably introduced to between 2500 rotations and 5000 rotations, inclusive, per 1 m, in order to form at least 7/cm microcrimp inflection points in the superfine polyester fiber, as with less than 2500 rotations the desired microcrimping will not be imparted, and with greater than 5000 rotations there will be generation of fluff or yarn breakage. A more preferred range for the false-twisting treatment conditions is between 3000 rotations and 4000 rotations, inclusive.

The superfine polyester fiber obtained by this method is used to produce a tubular seamless fabric. The loom used to produce the tubular seamless fabric is not particularly restricted, and the use of a shuttle loom in which the weft yarn is passed through by reciprocal movement of a shuttle is preferred because it can minimize reduction in woven density at the tab sections of the woven fabric (the folded sections of the tubular woven fabric), and result in a uniform woven fabric thickness. When fibers with a relatively large single filament fineness and total fineness are used to prepare a sack-like woven fabric with a large thickness and wide woven width, such as for an air bag, a shuttleless weaving machine such as an air jet loom, water jet room or rapier loom may be used, but when a low-thickness, high-density uniform woven fabric such as according to the invention is prepared with a shuttleless weaving machine, the woven density is notably decreased at the tab sections of the woven fabric causing partial increase in water permeability, and therefore endoleak and the like become crucial defects when it is utilized as a stent graft fabric.

Also, for preparation of the tubular seamless fabric of the invention, it is preferred to use a full width temple for the purpose of stabilization cloth fell, uniformity of the thickness and diameter of the woven fabric, and minimizing yarn breakage during processing. Since the tubular seamless fabric of the invention employs superfine polyester fiber and has a very thin thickness, when a full width temple is used it preferably has a structure with minimal contact area between the woven fabric and full width temple, or it is preferred to select a material with a low frictional coefficient for the full width temple member at the section contacting with the woven fabric, for the purpose of minimizing abrasion of the woven fabric by the full width temple. An appropriate design may be selected for the structure of the full width temple and the frictional coefficient of the member, according to the single filament fineness or total fineness of the superfine polyester fiber used and the woven density of the warp yarn or weft yarn.

When the tubular seamless fabric is prepared, it is necessary to control raising and lowering of the warp yarn or and for this purpose the apparatus used may be a Jacquard opening apparatus or dobby opening apparatus.

After weaving, it is preferred to carry out scouring treatment to remove the lubricant and heat setting to stabilize the form. Also, the tubular seamless fabric may be subjected to calendering treatment to further reduce the thickness of the fabric, in which case press working that may crush the tubular seamless fabric must be avoided. When a tubular woven fabric is pressed with a pressing machine, wrinkles are created in the longitudinal direction at the tab sections, and when it is indwelling as a stent graft in a blood vessel, endoleak occurs from the wrinkle sections and it cannot effectively function as a stent graft. When calendering treatment is carried out, preferably a cylindrical bar designed to match the diameter of the tubular seamless fabric is inserted in the tubular seamless fabric, the cylindrical bar is set in the pressing machine, and the entire tubular seamless fabric is subjected to press treatment while rotating the cylindrical bar, and heat setting and calendering treatment may also be carried out simultaneously in such a system. Selection of the heat setting temperature or calendering treatment conditions (temperature, pressure, etc.) is preferably such that the conditions are set for water permeability after needle puncture of the tubular seamless fabric following treatment, i.e. water permeability after needle puncture, not exceeding 300 cc/cm$^2$/min. For example, when a woven fabric has been treated with a strong pressing force that crushes it into a film, a large open needle hole remains from combination with the stent, and the water permeability increases.

A tubular seamless fabric prepared by the method described above can be combined with a stent using suture thread and inserted into a catheter for use as a stent graft.

The present invention will now be explained in more specific detail, with the understanding that the invention is in no way limited by the following examples.

The major values for the physical properties were measured by the following methods.

(1) Reduced Viscosity ($\eta sp/c$)

The reduced viscosity ($\eta sp/c$) is measured in the following manner.

A dilute solution of 0.35 g of polyethylene terephthalate (PET) sample dissolved in 0.25 deciliter of 1,1,1,3,3,3-hexafluoro-2-propanol (HFIP) is prepared at room temperature.

A Ubbellohde viscosity tube (tube diameter: 0.03) is used to measure the number of seconds of dropping of the dilute solution and HFIP solvent at 25° C., and the relative viscosity ($\eta sp$) is determined.

The relative viscosity ($\eta sp$) is divided by the polymer concentration C (g/dl) and the reduced viscosity $\eta sp/c$ is calculated.

(2) Component Content P Other than PET (a) Content $P_1$ of residual components adhering on fiber surface After cutting to a length of 1 cm for fiber or cutting to a 1 cm-square for a fabric, it is loosened into a fibrous form and scoured for 30 minutes with hot water at 95° C. to remove the spinning oil solution and then dried at 105° C. for 3 hours, and the weight ($W_0$) is measured. The fibrous substance is treated at 80° C.×45 minutes with a 3% sodium hydroxide aqueous solution with a liquor to goods ratio of 100, subjected to filtration and rinsing repeated 3 times with purified water and dried at 105° C.×3 hours, and the weight ($W_1$) is measured, and then the content of residual components adhering to the fiber surface is calculated by the following formula.

$$P_1(wt\%)=(W_0-W_1)/W_0 \times 100$$

(b) Content $P_2$ of residual components adhering to surface even after treatment in (a), and/or components copolymerized with PET The fibrous substance treated in (a) was dissolved in d-1,1,1,3,3,3-hexafluoro-2-propanol to 1-2 vol % (room temperature) and measured using $^1$H-NMR (AVANCEII AV400 M by Bruker BioSpin K.K.). The presence of signals other than for the PET component is confirmed from the NMR chart, and when a signal other than for the PET component is observed, the fiber surface-adhering component and/or copolymerizing component is identified and the content ($P_2$) is calculated from the NMR chart.

The value from (a) and (b) are summed to obtain the content P for components other than PET.

(3) Total Fineness/Single Filament Fineness

The total fineness (dtex) is the value obtained by winding the fiber bundle 50 times around a skein with a 1 m circumference, measuring the weight of the yarn and multiplying the value by 200. The single filament fineness (dtex) is the value of the total fineness determined by the method described above, divided by the filament number.

(4) Tensile Strength/Tensile Elongation/Toughness Parameter X

The tensile strength and tensile elongation were measured according to JIS-L-1013.

The toughness parameter X is determined by the following formula, using the value of the total fineness and single filament fineness determined in (3) above, and the tensile strength and tensile elongation determined by the method described above.

$$X=(\text{Tensile strength} \times \sqrt{\text{tensile elongation}})/(\text{total fineness} \times \text{single filament fineness})$$

(5) Interfilament Variation $Y_{(1-10)}$

A 1 cm portion of the fiber bundle is sampled at 10 points at equal spacings along 3 m in the fiber axis direction, and each fiber bundle is further divided into 3-10 portions and thinly spread out on the sample stage of a scanning electron microscope (SEM) for SEM observation at a magnification corresponding to 500 to 5000×. Lines are drawn on the obtained SEM photograph in the fiber bundle direction and the direction perpendicular thereto, the diameters of the monofilaments (fiber sizes) crossing the lines are directly measured from the enlarged image, and this procedure is carried out for a number of filaments corresponding to at least 30% of the total number of filaments. The interfilament variation Y is calculated by the following formula, based on the overall measurement results. This procedure is repeated for 10 sampled fiber bundle points, to obtain the interfilament variation $Y_{(1-10)}$ for the 10 values $Y_{(1-10)}$.

$$Y_{(1\sim10)}\sqrt{\frac{\Sigma(d_i-d_{av})^2}{(n-1)}} \qquad \text{[Formula 4]}$$

For preparation and SEM observation of the sample, the number of divisions of each fiber bundle and the magnification for observation may be selected as desired depending on the total number of fibers and the single filament fineness, but the standard for selection is 20-30 fibers per image.

(6) Size Unevenness (U %) in Fiber Axis Direction

The size unevenness (U %) in the fiber axis direction of the fiber bundle is measured under the following conditions, using an Evenness Tester Model KET-80C by Keisokki Kogyo Co., Ltd.

(Measuring conditions)
rreg: U %
Service selector: Normal
Range of scale: ±12.5%
Mat. speed: 50 m/min
Diagram speed: 10 cm/min (7) Burst Strength of Woven Fabric The woven fabric was subjected to a burst strength test based on ANSI/AAMI/ISO 7198:1998/2001 with n=5, and the average value for the maximum test strength is recorded.

(8) Water Permeability Before and after Woven Fabric Needle Puncture

The water permeability is measured before and after woven fabric needle puncture, according to ANSI/AAMI/ISO 7198:1998/2001. The water permeability test after needle puncture is the value measured after arbitrarily passing a tapered ⅜ needle 10 times through the fabric in a 1 cm² area. Measurement is conducted with n=5 both before and after needle puncture, and the average value is recorded.

(9) Woven Fabric Thickness

The thickness of the fabric is measured using a thickness gauge with a 1N load with n=5, and the average value is recorded.

(10) Cell Adhesion

The fabric is cut to a 1.5 cm-square and placed on a polystyrene 12-well plate, 1 ml of a suspension of rat fibroblasts ($10^4$ cell/ml) is added and culturing is conducted for 24 hours. The fabric was transferred to a base material for staining and subjected to fluorescent immunostaining, and the state of fluorescence of the cells was observed under a fluorescent microscope, visually evaluating the condition of cell adhesion onto the fabric by the following criteria.

VG: Cell adhesion found over entire fabric surface.
G: Some locations without cell adhesion found over the entire fabric surface.
F: Some locations with cell adhesion found over the entire fabric surface.
P: Virtually no locations with cell adhesion found over the entire fabric surface.

(11) Microcrimp Inflection Points

The microcrimp bending points are the number of microcrimps on average at 5 locations, as observed with the fibers in a state without tension and with a magnifying glass at 10× magnification. The inflection point of a crimp is an inflection point which is bent, undulating, arc-shaped, coiled, twisted, warped, zigzag, raised, depressed or spiraled, i.e. a non-linear condition of the superfine fiber. For example, when the crimping is undulating it is referred to as an undulating point of inflection, when the crimp is coiled the point at 180° revolution from an arbitrary point is defined as the inflection point, and an inflection point is defined to be present for every 180° revolution thereafter.

(12) Pososity (Void Percentage)

A fabric is embedded with a resin such as Technovit (Kulzer Co. Germany), a 3 μm-thick strip is prepared using a glass knife, and a photograph is taken with an optical microscope at 400× magnification. The porosity is calculated by the following formula, from area measurement at the fiber sections and fiber gap sections on the photograph. The image area measurement is accomplished using common image processing computer software, such as NIH Image.

Porosity (%)=(area occupied by superfine fiber bundles−area occupied by individual superfine fibers)/(area occupied by superfine fiber bundles)×100

Examples 1 to 11 and Comparative Examples 1 to 4

Polyethylene terephthalate (PET) was used for the starting material, and melt spinning was performed to wind up 65 dtex/300 F undrawn yarn.

The properties of the starting PET polymerized with germanium catalyst were as follows.

Reduced viscosity (ηsp/c): 1.162 dl/g
Titanium content: 2 ppm
Diethylene glycol content: 0.8 wt %
Oligomer content: 1.2 wt %

The spinneret used was a spinneret having 5 rows with 60 discharge nozzles (hole diameter: 0.08 mmφ) bored in a circumferential manner per circle (each with 60 discharge nozzles) (number of nozzles: 300), with a distance of 1.7 mm between discharge nozzles on the innermost row and a distance of 8 mm between all the rows. Cooling of the yarn was accomplished basically using a cooling air blasting apparatus with an air diffuser at an elevation angle of 37°.

Spinning was otherwise carried out under the conditions described in Table 1, and 65 dtex undrawn yarn was taken up for 2 hours at 2000 m/min. During this time, a high-speed camera was used to observe the condition of yarn breakage directly under the spinneret.

TABLE 1

| | Spinneret | | | Cooling conditions | | | | |
|---|---|---|---|---|---|---|---|---|
| | Spinneret surface temperature (° C.) | surface temperature distribution (° C.) | Hot zone*1 Length (mm) | Cooling air temperature*2 (° C.) | Cooling air speed (m/s) | Speed variation Z*3 — | Bundling location*4 (cm) | Spinnability |
| Example 1 | 303 | 3 | 36 | 13 | 1.0 | 0.07 | 26.5 | No yarn breakage, undrawn yarn taken up stably for 2 hours |
| Example 2 | 308 | 4 | 41 | 13 | 1.0 | 0.07 | 26.5 | Same as above |
| Example 3 | 300 | 3 | 34 | 13 | 1.0 | 0.07 | 26.5 | Same as above |
| Example 4 | 302 | 3 | 32 | 3 | 1.0 | 0.07 | 26.5 | Same as above |
| Example 5 | 305 | 4 | 43 | 13 | 0.7 | 0.08 | 26.5 | Yarn breakage once near innermost row, but with no other problems |
| Example 6 | 300 | 3 | 30 | 13 | 1.4 | 0.04 | 26.5 | Yarn breakage twice near outermost row, but with no other problems |

TABLE 1-continued

| | Spinneret | | | Cooling conditions | | | | |
|---|---|---|---|---|---|---|---|---|
| | Spinneret surface temperature (° C.) | surface temperature distribution (° C.) | Hot zone*1 Length (mm) | Cooling air temperature*2 (° C.) | Cooling air speed (m/s) | Speed variation Z*3 — | Bundling location*4 (cm) | Spinnability |
| Example 7 | 303 | 3 | 36 | 13 | 1.0 | 0.02 | 26.5 | No yarn breakage, undrawn yarn taken up stably for 2 hours |
| Example 8 | 302 | 3 | 37 | 13 | 1.0 | 0.13 | 26.5 | Yarn breakage 2 times, but with no other problems |
| Example 9 | 308 | 3 | 39 | 3 | 1.0 | 0.07 | 22.0 | Same as above |
| Example 10 | 305 | 4 | 54 | 20 | 1.0 | 0.07 | 26.5 | Yarn breakage 5 times, but undrawn yarn was taken up |
| Example 11 | 304 | 6 | 57 | 13 | 0.5 | 0.07 | 26.5 | Yarn breakage 6 times, but undrawn yarn was taken up |
| Comp. Ex. 1 | 284 | 7 | (Unmeasurable) | 13 | 1.0 | 0.07 | 26.5 | Considerable yarn breakage, not possible to sample undrawn yarn |
| Comp. Ex. 2 | 323 | 3 | (Unmeasurable) | 13 | 1.0 | 0.07 | 26.5 | Considerable yarn breakage, not possible to sample undrawn yarn |
| Comp. Ex. 3 | 301 | 3 | (Unmeasurable) | 13 | 2.2 | 0.07 | 26.5 | Considerable yarn breakage, not possible to sample undrawn yarn |
| Comp. Ex. 4 | 303 | 3 | (Unmeasurable) | 13 | 0.9 | 0.20 | 26.5 | Considerable yarn breakage, not possible to sample undrawn yarn |

Hot zone*1: Zone controlled to an atmosphere temperature of 150° C. or higher (perpendicular distance from center section of spinneret surface)
Cooling air temperature*2: Temperature of cooling air blasted from cooling air blasting apparatus (using a thermoheater for temperature adjustment of cooling air)
Speed variation Z*3: Value represented as standard deviation for variation of speed of cooling air blasted from cooling air blasting surface
Bundling location*4: Location where discharged fiber bundles are bundled Examples 1 to 9 all allowed take-up for 2 hours. Examples 10 and 11 exhibited yarn breakage several times, but take up of the undrawn yarn was possible. Comparative Examples 1 to 4 exhibited considerable yarn breakage, and sampling of the undrawn yarn was not possible. Also, Comparative Examples 3 and 4 allowed sampling of the undrawn yarn, but considerable yarn breakage occurred and stable spinning was not possible.

The undrawn yarns taken up in Examples 1 to 9 and Comparative Examples 3 and 4 were subjected to drawing heat treatment with a drawing machine comprising a known heated roll, with a first roll temperature of 75° C. and a second roll temperature of 130° C., to a target tensile elongation of 30%, to obtain a superfine polyester fiber.

The content of components other than PET in the obtained superfine polyester fiber was less than 2 wt % in all cases. The reduced viscosity and other physical properties are shown in Table 2.

TABLE 2

| | Superfine polyester fiber properties | | | | | | | | |
|---|---|---|---|---|---|---|---|---|---|
| | Reduced viscosity (dl/g) | Total fineness (dtex) | Single filament fineness (dtex) | Tensile strength (cN/dtex) | Tensile elongation (%) | Toughness | Toughness parameter X | Variation between monofilaments Y*1 | U % (%) |
| Example 1 | 0.980 | 39.4 | 0.13 | 4.7 | 32 | 26.6 | 5.1 | 0.23 | 1.0 |
| Example 2 | 0.961 | 38.9 | 0.13 | 4.9 | 33 | 28.2 | 5.6 | 0.22 | 1.2 |
| Example 3 | 0.988 | 39.2 | 0.13 | 4.5 | 31 | 25.1 | 4.9 | 0.25 | 1.7 |
| Example 4 | 0.978 | 39.2 | 0.13 | 4.9 | 31 | 27.3 | 5.3 | 0.20 | 0.8 |
| Example 5 | 0.980 | 39.1 | 0.13 | 4.6 | 32 | 26.0 | 5.1 | 0.36 | 1.6 |
| Example 6 | 0.989 | 39.2 | 0.13 | 4.7 | 31 | 26.0 | 5.1 | 0.20 | 1.8 |
| Example 7 | 0.985 | 39.2 | 0.13 | 4.8 | 31 | 26.7 | 5.2 | 0.19 | 1.0 |
| Example 8 | 0.979 | 39.4 | 0.13 | 4.6 | 30 | 25.2 | 4.9 | 0.41 | 1.3 |
| Example 9 | 0.968 | 39.1 | 0.13 | 5.0 | 32 | 28.3 | 5.6 | 0.18 | 0.8 |
| Example 10 | 0.970 | 39.2 | 0.13 | 3.9 | 27 | 20.3 | 4.0 | 0.81 | 5.8 |
| Example 11 | 0.982 | 38.9 | 0.13 | 4.2 | 29 | 22.6 | 4.5 | 0.73 | 3.6 |

*1Y value of sample with largest numerical value among samples Y1 to Y10

Examples 12 and 13, and Comparative Example 5

Superfine polyester fiber was obtained by taking up undrawn yarn and drawing heat treatment of the undrawn yarn in the same manner as Example 1, except for using the reduced viscosity PET polymer shown in Table 3 as the starting material. The content of components other than PET in the superfine polyester fiber was less than 2 wt % in all cases. The reduced viscosity and other physical properties are shown in Table 3. The superfine polyester fiber of Comparative Example 5 had low reduced viscosity and breaking strength below 3.5 cN/dtex.

examples, having a tensile strength of 4.5 cN/dtex and a tensile elongation of 32%. Examples 20 to 24 had no fluff and satisfactory suitability for the textile processing steps, and the obtained fabrics were able to satisfy all of the target physical properties (thickness, burst strength, water permeability and catheter insertability). Also, the variation in woven fabric thickness was in the range of ±2% to 10% for all of the examples, and therefore the thickness uniformity was excellent.

Comparative Example 10, on the other hand, had considerable yarn breakage during the textile processing steps, and a fabric could not be obtained. Presumably, the low tensile

TABLE 3

| | Superfine polyester fiber properties | | | | | | | | | |
|---|---|---|---|---|---|---|---|---|---|---|
| | Stating PET reduced viscosity (dl/g) | Reduced viscosity (dl/g) | Total fineness (dtex) | Single filament fineness (dtex) | Tensile strength (cN/dtex) | Tensile elongation (%) | Toughness | Toughness parameter X | Variation between monofilaments Y*[1] | U % (%) |
| Example 12 | 0.977 | 0.830 | 39.0 | 0.13 | 3.6 | 30 | 19.7 | 3.9 | 0.27 | 2.1 |
| Example 13 | 1.280 | 1.001 | 39.2 | 0.13 | 5.4 | 31 | 30.1 | 5.9 | 0.26 | 1.2 |
| Comp. Ex. 7 | 0.863 | 0.723 | 38.3 | 0.13 | 3.2 | 28 | 16.9 | 3.5 | 0.69 | 3.6 |

*[1]Y value of sample with largest numerical value among samples Y1 to Y10

Examples 14 to 19 and Comparative Examples 6 to 9

Superfine polyester fiber was obtained in the same manner as Example 2, except that melt spinning was carried out with the spinneret selected for uptake of the undrawn yarn shown in Table 4 and with the cooling air temperature set to 10° C., and also with the draw ratio arbitrarily set. The physical properties of the obtained superfine polyester fiber are shown in Table 4.

elongation rendered it unable to withstand abrasion and impact during the textile processing steps, and resulted in considerable yarn breakage.

In Comparative Example 11, a fabric was obtained but the tensile strength of the superfine polyester fiber used for the weft yarn was low at less than 3.5 cN/dtex, while it was not possible to sufficiently increase the woven density, and the burst strength of the fabric could not reach the target 10 kg. In Comparative Example 12, the single filament fineness of the superfine polyester fiber used for the weft yarn was large

TABLE 4

| | Superfine polyester fiber properties | | | | | | | | | |
|---|---|---|---|---|---|---|---|---|---|---|
| | Undrawn yarn (total fineness/number of filaments) | Draw ratio (factor) | Reduced viscosity (dl/g) | Total fineness (dtex) | Single filament fineness (dtex) | Tensile strength (cN/dtex) | Tensile elongation (%) | Toughness | Toughness parameter X | Variation between monofilaments Y*[1] |
| Example 14 | 65 dtex/300 F | 1.50 | 0.983 | 43.1 | 0.14 | 4.7 | 42 | 30.5 | 4.9 | 0.21 |
| Example 15 | 120 dtex/450 F | 1.60 | 0.991 | 72.4 | 0.16 | 4.8 | 34 | 28.0 | 2.4 | 0.25 |
| Example 16 | 48 dtex/150 F | 1.60 | 0.975 | 30.3 | 0.20 | 5.0 | 29 | 26.9 | 4.4 | 0.18 |
| Example 17 | 48 dtex/150 F | 1.25 | 0.977 | 36.9 | 0.25 | 4.6 | 38 | 28.4 | 3.1 | 0.19 |
| Example 18 | 32 dtex/150 F | 1.60 | 0.945 | 20.1 | 0.13 | 4.9 | 32 | 27.7 | 10.3 | 0.17 |
| Example 19 | 32 dtex/150 F | 1.25 | 0.944 | 25.8 | 0.17 | 4.4 | 41 | 28.2 | 6.3 | 0.17 |
| Comp. Ex. 6 | 65 dtex/300 F | 1.75 | 0.981 | 36.9 | 0.12 | 4.9 | 11 | 16.3 | 3.6 | 0.20 |
| Comp. Ex. 7 | 30 dtex/150 F | 0.00 | 0.944 | 32.1 | 0.21 | 2.7 | 141 | 32.1 | 4.7 | 0.19 |
| Comp. Ex. 8 | 120 dtex/100 F | 1.60 | 0.989 | 76.1 | 0.76 | 5.0 | 33 | 28.7 | 0.5 | 0.25 |
| Comp. Ex. 9 | 210 dtex/450 F | 1.60 | 1.010 | 130.7 | 0.29 | 4.4 | 30 | 24.1 | 0.6 | 0.43 |

*[1]Y value of sample with largest numerical value among samples Y1 to Y10

Examples 20 to 24 and Comparative Examples 10 to 14

The warp yarn and weft yarn shown in Table 5 were used to form a plain weave tubular seamless fabric with an inner diameter of 50 mm, using a shuttle weaving machine and a Jacquard opening apparatus. The woven fabrics were finished by scouring and heat setting. The woven density and the evaluation results for the obtained fabrics are shown below in Table 5. The regular fiber used here was the starting PET polymer used in all of the examples and comparative at 0.76 dtex, and therefore the fiber bundle did not spread out thinly during the textile processing steps and the thickness of the fabric exceeded the target 90 μm, making it unable to pass through a 6 mm hole. Also, in Comparative Example 13, the single filament fineness of the superfine polyester fiber was smaller than 0.5 dtex, but since the total fineness was 130 dtex which exceeded the upper limit specified by the invention, the thickness of the fabric exceeded the target 90 μm, making it unable to pass through a 6 mm hole. In Comparative Example 14, both the warp yarn and weft yarn had single filament fineness significantly exceeding 0.5 dtex, and therefore although the woven fabric thickness was 85 μm, it was unable to pass through a 6 mm hole. In addition, the water permeability increased after needle puncture, raising concerns in terms of practical performance.

properties (thickness, burst strength, water permeability and catheter insertability). In addition, the porosity of the fabric was 48%, and in the evaluation of cell adhesion, cell adhesion was found over the entire fabric surface.

TABLE 5

| | Warp yarn | | Weft yarn | | Woven density | | Woven fabric evaluation | |
|---|---|---|---|---|---|---|---|---|
| | Yarn type | (total fineness/ single filament fineness) | Yarn type | (total fineness/ single filament fineness) | Warp density (no./cm) | Weft density (no./cm) | Super fine structure ratio (%) | Thickness (μm) |
| Example 20 | Example 1 | 39.4/0.13 | Example 1 | 39.4/0.13 | 191 | 114 | 100.0 | 74 |
| Example 21 | Regular fiber | 34.1/1.42 | Example 1 | 39.4/0.13 | 211 | 114 | 38.5 | 78 |
| Example 22 | Regular fiber | 34.1/1.42 | Example 16 | 30.3/0.20 | 203 | 137 | 37.5 | 69 |
| Example 23 | Regular fiber | 34.1/1.42 | Example 15 | 72.4/0.16 | 206 | 102 | 51.2 | 88 |
| Example 24 | Regular fiber | 34.1/1.42 | Example 18 | 20.1/0.13 | 206 | 178 | 33.7 | 55 |
| Comp. Ex. 10 | Regular fiber | 34.1/1.42 | Comp. Ex. 6 | 36.9/0.12 | — | — | — | — |
| Comp. Ex. 11 | Regular fiber | 34.1/1.42 | Comp. Ex. 7 | 32.1/0.21 | 211 | 86 | 28.0 | 69 |
| Comp. Ex. 12 | Regular fiber | 34.1/1.42 | Comp. Ex. 8 | 76.1/0.76 | 206 | 89 | 49.1 | 101 |
| Comp. Ex. 13 | Regular fiber | 34.1/1.42 | Comp. Ex. 9 | 130.7/0.29 | 208 | 76 | 58.4 | 117 |
| Comp. Ex. 14 | Regular fiber | 34.1/1.42 | Regular fiber | 34.1/1.42 | 208 | 114 | 0.0 | 85 |

| | Woven fabric evaluation | | | | |
|---|---|---|---|---|---|
| | Burst strength (N) | Water permeability before needle puncture (cc/cm$^2$/min) | Water permeability after needle puncture (cc/cm$^2$/min) | Catheter insertability 6 mm hole | Cell adhesion |
| Example 20 | 181 | 129 | 132 | G | VG |
| Example 21 | 216 | 140 | 157 | G | G |
| Example 22 | 203 | 108 | 136 | G | G |
| Example 23 | 299 | 99 | 108 | G | G |
| Example 24 | 152 | 66 | 113 | G | G |
| Comp. Ex. 10 | — | — | — | — | — |
| Comp. Ex. 11 | 72 | 551 | — | G | F |
| Comp. Ex. 12 | 302 | 228 | 261 | P | P |
| Comp. Ex. 13 | 326 | 191 | 220 | P | F |
| Comp. Ex. 14 | 209 | 177 | 306 | P | P |

Example 25

The superfine polyester fiber obtained in Example 1 was subjected to false twisting at 4000 turns per 1 m, to obtain a false twisted yarn with 25/cm microcrimp bending points. A fabric was formed under the same conditions as Example 19 except for using false twisted yarn as the weft yarn. The obtained fabrics were able to satisfy all of the target physical Comparative Example 15

A sea-island composite polyester fiber was obtained as a sea-island composite polyester fiber with a total fineness of 120 dtex and 24 filaments (number of island components in filament: 24), by spinning and drawing fibers composed of copolymerized PET comprising PET for the sea component and terephthalic acid and 5-sodiumsulfoisophthalic acid as acid components other than polyester for the island component (sea component and island component weight ratio=10/90), by a known method. The sea-island composite polyester fiber was used as the warp yarn and weft yarn to form a plain weave tubular woven fabric with an inner diameter of 50 mm and a warp density/weft density ratio of 140/89 (per inch), and after removing the sea component by treatment with a 3% sodium hydroxide aqueous solution at 90° C. ×45 minutes, it was rinsed and dried to obtain a fabric composed of a sea-island superfine polyester fiber having a total fineness of 75 dtex and a single filament fineness of 0.13 dtex. The fabric composed of the sea-island superfine polyester fiber was again subjected to alkali treatment, rinsing and drying by the methods described above, for evaluation of the content $P_1$ of components other than PET residually adhering to the fiber surfaces. Also, the content $P_2$ of components residually adhering to the surface even after alkali treatment and/or components copolymerized with PET was evaluated by NMR.

The $P_1$ value of the fabric composed of the sea-island superfine polyester fiber was 2.3 wt %. Also, a signal was found in NMP for an isophthalic acid component, which was surmised to be 5-sodiumsulfoisophthalic acid that had not been removed by alkali treatment and was residually adhering to the fiber surfaces. Assuming that the isophthalic acid component detected by NMR was 5-sodiumsulfoisophthalic acid, the $P_2$ value for the fabric composed of the sea-island superfine polyester fiber is 0.3 wt %. Thus, components other than PET remained at 2 wt % or greater in the fabric composed of the sea-island superfine polyester fiber.

INDUSTRIAL APPLICABILITY

A superfine polyester fiber composed essentially of a PET component, according to the invention, does not involve concerns regarding residual substances from the sea component or solvent, such as with sea-island superfine fibers or polymer blend-type superfine fibers, and can meet the requirements for thinness and high burst strength demanded of stent graft fabrics and artificial blood vessels, and it can therefore be suitably utilized as a material for implantation into the human body such as a stent graft fabric or artificial blood vessel. Furthermore, when the tubular seamless fabric of the invention is to be used as a stent graft fabric, the stent graft may have a low profile, and it can therefore reduce the physical and economical burden on patients, such as shortening the inpatient periods, and can reduce risks such as vascular wall damage. In addition, it is possible to widen the range of applications to cases that have hitherto been excluded as targets of transcatheter intravascular treatment, such as females and Asians that have narrower arteries.

What is claimed is:

1. A fabric having a plain weave structure or twill weave structure of a superfine polyester fiber and comprising at least 20 wt % of said superfine polyester fiber, said superfine polyester fiber having a polyethylene terephthalate component content of 98 wt % or greater, and satisfying the following requirements:

(1) a reduced viscosity ($\eta sp/c$) of 0.80 dl/g or greater,
   (2) a total fineness of between 7 dtex and 120 dtex, inclusive, and a single filament fineness of 0.5 dtex or less,
   (3) a toughness parameter X of 2.0 or greater as represented by the following formula (1):

$$X=(\text{tensile strength} \times \sqrt{\text{tensile elongation}})/(\text{total fineness} \times \text{single filament fineness})$$

Formula (1), wherein tensile strength is expressed in CN/dtex, tensile elongation is expressed in %, and fineness is expressed in dtex,
   a tensile strength of 3.5 cN/dtex or greater and a tensile elongation of 12% or greater;
   wherein the fabric has a thickness of between 10 µm and 90 µm, inclusive.

2. A fabric according to claim 1, wherein said superfine polyester fiber further satisfies the following requirement:

(4) For each of 10 sampled fiber bundles, where 10 fiber bundles of 1 cm are sampled at equal spacings of 3 m in the yarn length direction, the interfilament variation $Y_{(1-10)}$ represented by the following formula (2):

$$Y_{(1\sim 10)} \sqrt{\frac{\sum (d_i - d_{av})^2}{(n-1)}} \tag{2}$$

wherein n is a number of filaments corresponding to at least 30% of the total number of filaments from each of 10 fiber bundles, the yarn diameter di is the diameter of each yarn among n filaments corresponding to at least 30% of the total number of filaments from each of 10 fiber bundles, and day is the average for n filaments, is 0.5 or less for all.

3. A stent graft fabric comprising the fabric according to claim 1 or 2.

4. An artificial blood vessel comprising the fabric according to claim 1 or 2.

5. An artificial fiber fabric comprising the fabric according to claim 1 or 2.

* * * * *

UNITED STATES PATENT AND TRADEMARK OFFICE
CERTIFICATE OF CORRECTION

PATENT NO. : 10,363,153 B2
APPLICATION NO. : 14/383353
DATED : July 30, 2019
INVENTOR(S) : Takahashi et al.

Page 1 of 1

It is certified that error appears in the above-identified patent and that said Letters Patent is hereby corrected as shown below:

In the Claims

Claim 2, Column 28, Lines 43-44, "and day is the average" should read -- and dav is the average --.

Signed and Sealed this
First Day of October, 2019

Andrei Iancu
*Director of the United States Patent and Trademark Office*